(12) United States Patent
Neilan

(10) Patent No.: US 7,837,703 B2
(45) Date of Patent: Nov. 23, 2010

(54) GUIDEWIRE FOR EMBOLIC DEVICE

(75) Inventor: John Neilan, Gort (IE)

(73) Assignee: Salviac Limited, Dublin (IE)

( * ) Notice: Subject to any disclaimer, the term of this patent is extended or adjusted under 35 U.S.C. 154(b) by 347 days.

(21) Appl. No.: 11/926,717

(22) Filed: Oct. 29, 2007

(65) Prior Publication Data
US 2009/0112253 A1    Apr. 30, 2009

(51) Int. Cl.
*A61M 29/00* (2006.01)
(52) U.S. Cl. ................................ 606/200
(58) Field of Classification Search ......... 606/200; 600/585
See application file for complete search history.

(56) References Cited

U.S. PATENT DOCUMENTS

| | | | |
|---|---|---|---|
| 5,303,714 A * | 4/1994 | Abele et al. | 600/585 |
| 5,833,644 A | 11/1998 | Zadno-Azizi et al. | |
| 6,179,859 B1 * | 1/2001 | Bates et al. | 606/200 |
| 6,344,049 B1 * | 2/2002 | Levinson et al. | 606/200 |
| 6,371,971 B1 * | 4/2002 | Tsugita et al. | 606/200 |
| 6,398,791 B1 * | 6/2002 | Que et al. | 606/127 |
| 2004/0010243 A1 * | 1/2004 | Klint | 604/526 |

* cited by examiner

*Primary Examiner*—Todd E Manahan
*Assistant Examiner*—Jonathan A Hollm
(74) *Attorney, Agent, or Firm*—Sughrue Mion, PLLC; Jonathan Feuchtwang

(57) ABSTRACT

A guidewire for use with an embolic protection filter and a method of deploying an embolic protection filter are provided. The guidewire includes a core wire; a core wire tip disposed at a distal end of the core wire; and a hypo shaft, coaxially disposed around the core wire, wherein the hypo shaft is moveable proximally and distally along the core wire with the core wire tip limiting a distal movement of the hypo shaft.

4 Claims, 5 Drawing Sheets

GUIDEWIRE FOR EMBOLIC DEVICE

BACKGROUND OF THE INVENTION

1. Field of the Invention

Devices consistent with the present invention relate to guidewires for catheters and, more particularly, to guidewires for use with low profile embolic protection devices deployed without the need for actuating delivery catheters.

2. Description of the Related Art

Arteriosclerosis, also known as atherosclerosis, is a common human ailment arising from the deposition of fatty-like substances, referred to as atheroma or plaque, on the walls of blood vessels. Such deposits occur in peripheral blood vessels that feed limbs of the body, coronary blood vessels that feed the heart, and in carotid blood vessels that feed the head, neck, and brain. Localized accumulation of deposits within regions of the blood vessels may result in stenosis, or narrowing of the vascular channel. When this occurs, blood flow is restricted and the person's health is at serious risk.

Numerous approaches for reducing and removing such vascular deposits have been proposed, including balloon angioplasty, in which a balloon-tipped catheter is used to dilate a stenosed region within the blood vessel; atherectomy, in which a blade or other cutting element is used to sever and remove the stenotic material; laser angioplasty, in which laser energy is used to ablate at least a portion of the stenotic material; and the like. Related art angioplasty catheters are well known for their utility in treating the build-up of plaque and other occlusions in blood vessels.

In order to facilitate the use of the various treatment devices, a related art guidewire is typically used to assist in moving these devices throughout the vasculature. The related art guidewire is thinner and more flexible than the deployment or retrieval catheters for the treatment devices. Therefore, the related art guidewire may more easily be manipulated through narrow or otherwise tortuous regions of the vasculature to reach the treatment area. The related art guidewire also provides a means for deploying an embolic protection device, i.e., a filter, downstream of the vasculature to filter any plaque or other occluded material which may become dislodged during treatment, and thus prevents the occlusion material from traveling through the blood vessels and becoming lodged in the brain or other smaller blood vessels preventing blood flow and causing a stroke or other damage. U.S. Pat. No. 6,336,934, which is herein incorporated by reference in its entirety, describes examples of such a related art procedure and example of the embolic protection devices.

Turning to FIGS. 1-5, the deployment of an embolic protection device using a related art guidewire is shown. As shown in FIGS. 1 and 2, the embolic protection device includes an arrangement of spokes 25 covered with a membrane or porous fabric or mesh 30 that can be folded down into a delivery sheath or pod for subsequent deployment in a target vessel. The design consists of a guidewire 10 onto which are radially or circumferentially bonded a series of pre-shaped wires 25. The wires 25 are joined on the proximal end into a movable collar or tube 15 mounted on the guidewire 10 and at the distal end into a tube 20 which is fixed to the guidewire 10. The tube 15 can move proximally and distally to the extent that it will open and close the assembly in a manner similar to an umbrella and thereby occlude the vessel, as shown in FIG. 2.

When the assembly is configured longitudinally a sheath or pod may be slid over it to cover it. A loaded catheter is positioned in a treatment area by threading it over the guidewire 10. Once the desired treatment area has been reached, the sheath may be moved back and allow the assembly be exposed in the vessel. As shown in FIGS. 3-5, an actuating sleeve 40 can then be moved forward to open or deploy the assembly. The relative sizing and choice of materials operates such that the actuating sleeve 40 will not slide on the guidewire 10 unless an external force is applied to move it. When deployed, the device will remain open and catch whatever embolic material is dislodged during treatment. At the end of the procedure, a pre-shaped component is advanced over the guidewire 10 and docks with the movable tube 15, allowing it to be slid towards the proximal end of the device with the result that the structure is closed. A larger sheath can then separately be advanced to the site of the filter and the filter may be pulled or manipulated proximally into it. When withdrawn into the sheath or catheter, the device may then be removed either over the guidewire 10 or with it.

The above related art guidewire has a number of disadvantages. First, advancements in the fabrication and use of embolic protection devices have resulted in embolic protection devices of extremely low profiles. This makes using an actuation sheath difficult. Moreover, it is desirable to be able to use an embolic protection device without the need for an actuating delivery catheter.

SUMMARY OF THE INVENTION

Exemplary embodiments of the present invention address the above disadvantages and other disadvantages not described above. Also, the present invention is not required to overcome the disadvantages described above.

An object of the present invention is to provide a guidewire for use with an embolic protection device which does not require an actuating delivery catheter.

According to an aspect of the present invention, there is provided a guidewire for use with an embolic protection filter, the guidewire including a core wire; a core wire tip disposed at a distal end of the core wire; and a hypo shaft, coaxially disposed around the core wire, wherein the hypo shaft is moveable proximally and distally along the core wire with the core wire tip limiting a distal movement of the hypo shaft.

According to another aspect of the present invention, there is provided a method of using a guidewire which includes a core wire, a core wire tip disposed at a distal end of the core wire, and a hypo shaft, moveably and coaxially disposed around the core wire, the method including sliding the hypo shaft along the core wire until a distal end of the hypo shaft meets the core wire tip; inserting the hypo shaft into a vasculature and moving the hypo shaft through the vasculature until a proximal end of the core wire tip is downstream of a treatment area; sliding the hypo shaft in a proximal direction from a proximal end thereof to form a filter location space between a distal end of the hypo shaft and the core wire tip; sliding a delivery sheath, containing an embolic protection device therein, coaxially along the hypo shaft until a proximal end of the embolic protection device passes a distal end of the hypo shaft; pulling the delivery sheath from a proximal end thereof to deploy the embolic protection device into the filter location space; and removing the delivery sheath from the vasculature.

BRIEF DESCRIPTION OF THE DRAWINGS

The above and other aspects of the present invention will become more apparent by describing in detail exemplary embodiments thereof with reference to the attached drawings, in which.

DESCRIPTION OF EXEMPLARY EMBODIMENTS OF THE PRESENT INVENTION

Hereinafter, exemplary embodiments of the present inventive concept will be described in detail with reference to the drawings. The same reference numbers are used to denote the same elements in different drawings.

Figure 1:
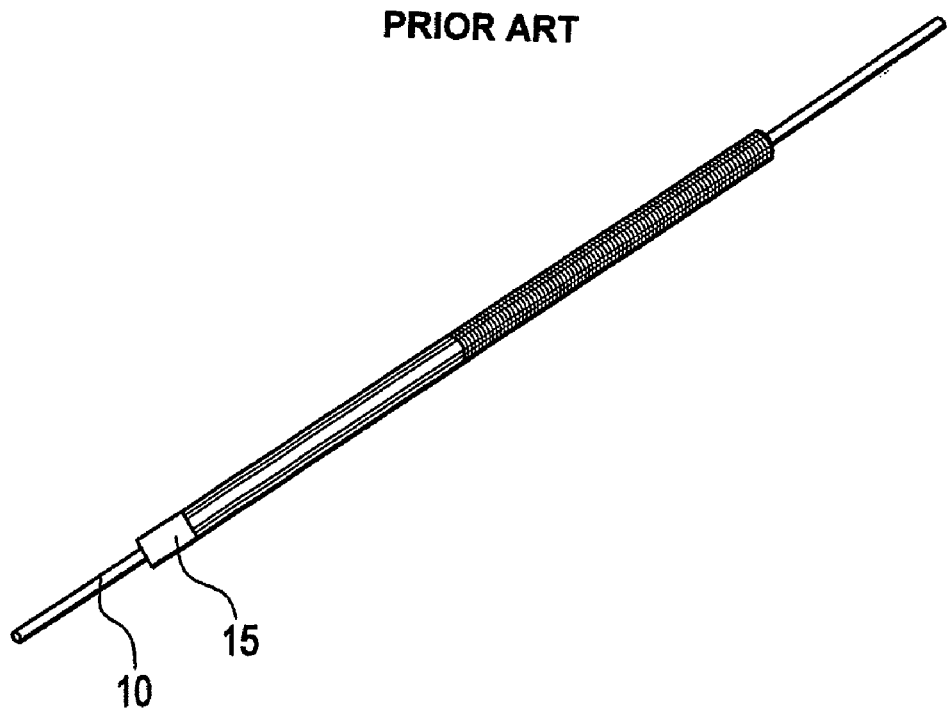
FIGS. 1 and 2 are views showing a related art embolic protection device in both an unexpanded and an expanded state, respectively.
Figure 2:
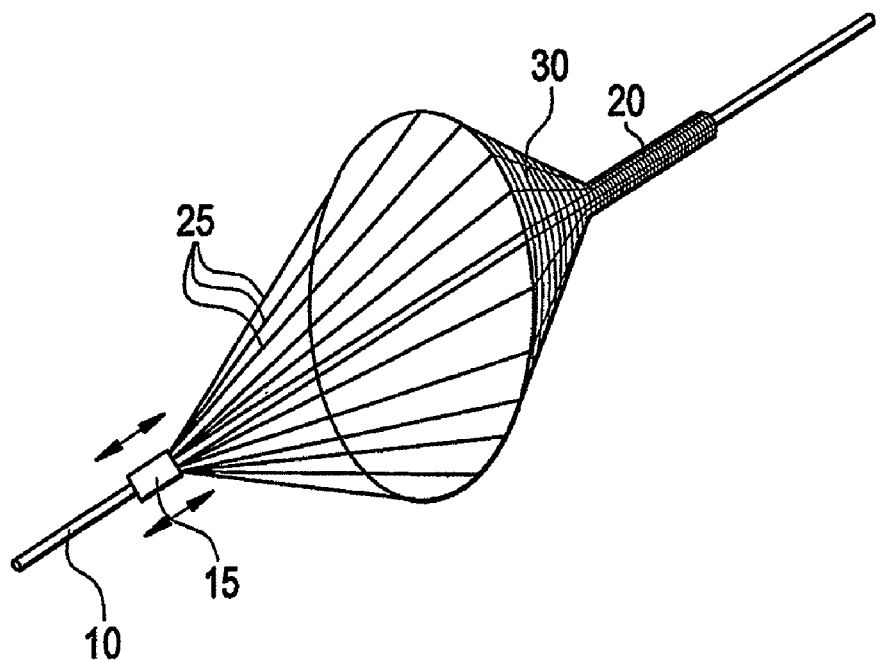
Figure 3:
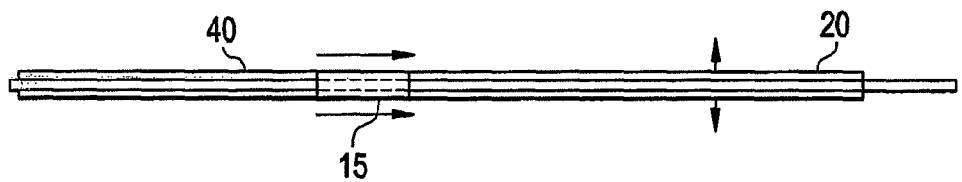
FIGS. 3-5 are views showing the deployment of the related art embolic protection device of FIGS. 1 and 2.
Figure 4:
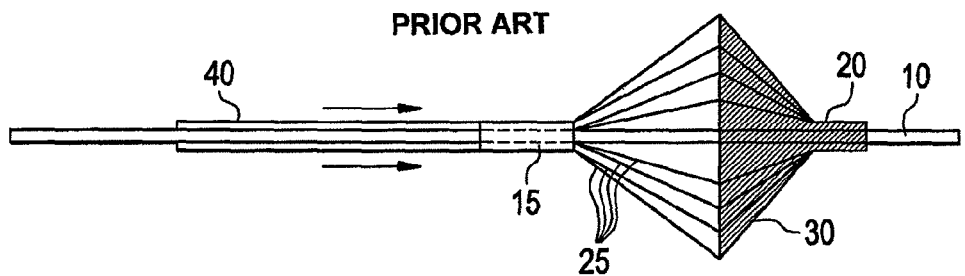
Figure 5:
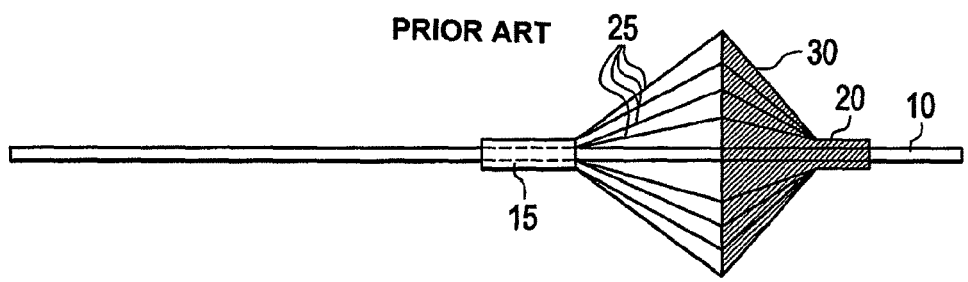
Figure 6:
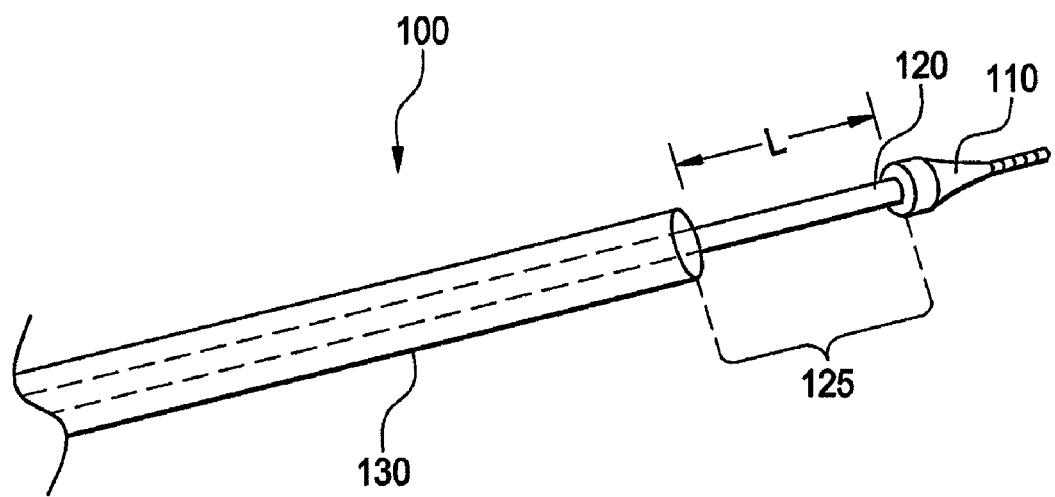
FIG. 6 is a view showing a guidewire according to an exemplary embodiment of the present invention.

Turning now to FIG. 6, a guidewire 100 according to an exemplary embodiment of the present invention is shown. The guidewire 100 includes a core wire 120, and a core wire tip 110 disposed at a distal end of the core wire 120. A hypo shaft 130, i.e. an outer guidewire shaft, is disposed coaxially around the core wire 120 such that the hypo shaft 130 may be slid back and forth proximally and distally along the core wire 120.

The core wire 120 is made of wire. However, optionally, the core wire 120 may be made of a polymer material. The core wire 120 may also contain a radiopaque marker to help identify the position of the core wire 120 in a vasculature.

Similarly, the hypo shaft 130 is made of wire, but may also be made of a polymer material. The hypo shaft 130 may also contain a radiopaque marker to help identify the position of the hypo shaft 130 in a vasculature.

The outer diameter of the guidewire 100 is from approximately 0.014" to approximately 0.035". One or both of the core wire 120 and the hypo shaft 130 may be tapered in at least one section in order to vary the stiffness of the guidewire 100. The core wire 120 or the hypo shaft 130 may also be replaced with a core wire 120 or hypo shaft of a more rigid or flexible material. In this way, a transition in stiffness of the wire and/or a filter assembly including the wire may be adjusted to suit an anatomical condition of a particular patient. For example, when moving the guidewire through a patient vasculature in order to locate the filter at a proper location to filter plaque and other occluded material, the core wire may be advanced further out of the hypo shaft in a telescoping manner to make the guidewire more pliable for maneuvering through tortuous passages of the vasculature, or alternatively the core wire may be withdrawn further into the hypo shaft in order to provide a more stiff, supportive guidewire.

In use, the hypo shaft 130 is pulled from the proximal end thereof in order to create a filter location space 125 (i.e., a "backwire") between the core wire tip and a distal end of the hypo shaft 130, as illustrated in FIG. 6.

Figure 7A:
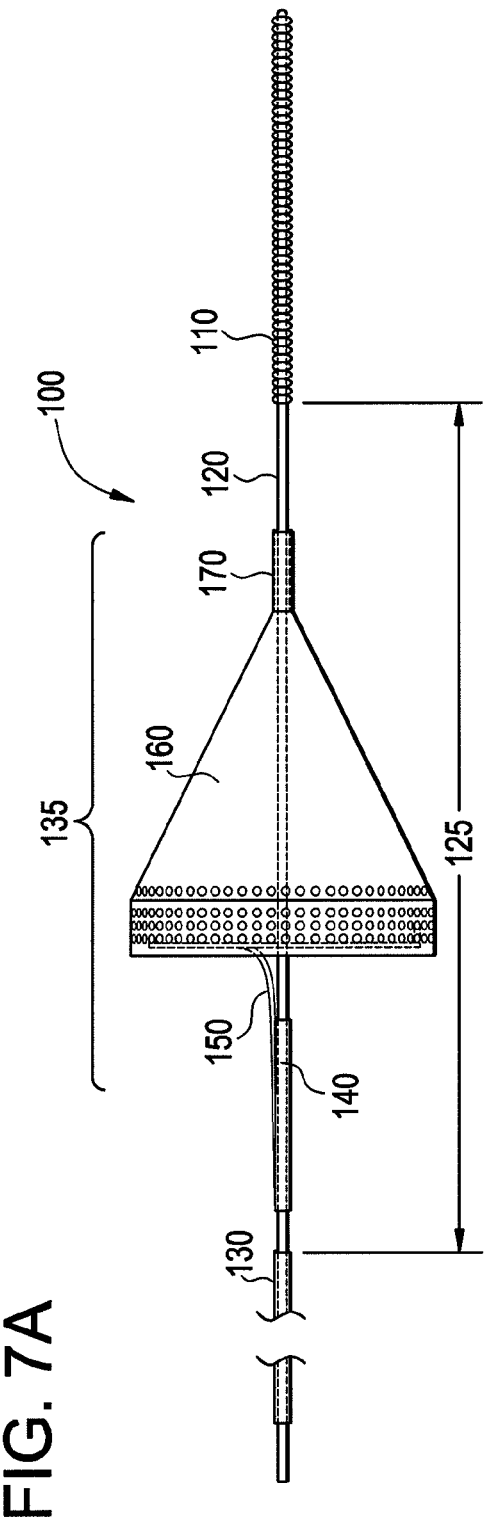
FIG. 7A is a view showing a filter element on the guidewire of FIG. 6.
Figure 7B:
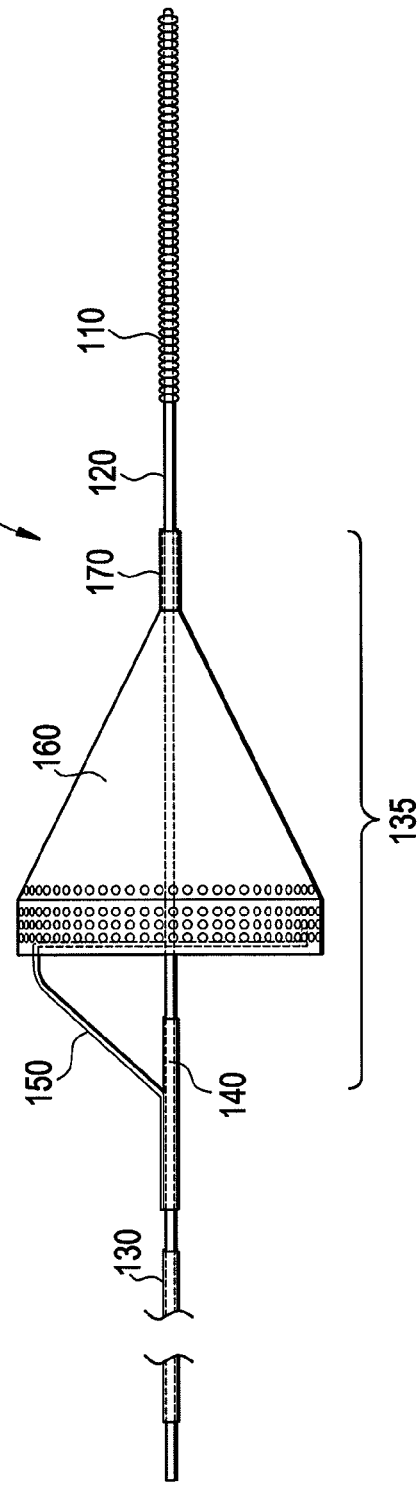
FIG. 7B is a view showing of the filter element and the guidewire of FIG. 7A with the filter element rotated axially ninety degrees.
Figure 7C:
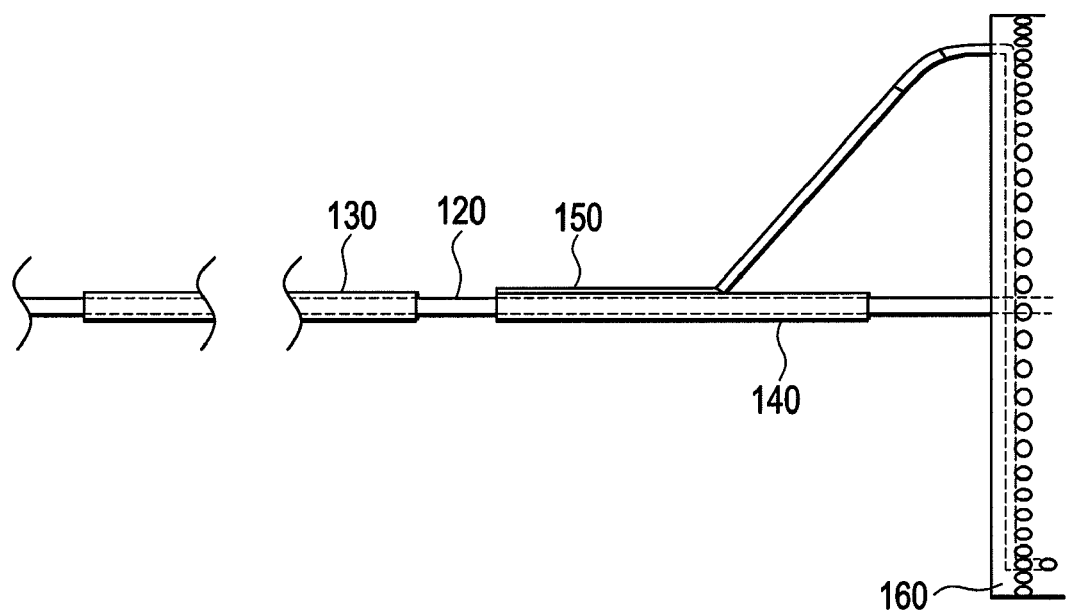
FIG. 7C is a close up view of a proximal end of the filter element on the guidewire in FIG. 7B.

FIGS. 7A and 7B are views showing a filter element on the guidewire of FIG. 6, with FIG. 7B showing the filter element rotated ninety degrees from the filter element in FIG. 7A. As shown in FIGS. 7A and 7B, a filter element 135 is slidably disposed on the core wire 120. The filter element 135 is of a type generally known in the related art. The filter element 135 includes a proximal filter core tube 140, a filter frame 150, a filter mesh 160, and distal filter core tube 170. In a collapsed state, the filter element 135 forms a very low profile and is of a diameter on the order of the core wire 120. As best shown in the close-up view of FIG. 7C, the filter frame 150 is attached to the proximal filter core tube 140 and to the distal filter core tube 170 such that the filter element 135 may slide freely, both proximally and distally, in the filter location space 125.

The guidewire 100 is used with an embolic protection device as follows. The distal filter core tube 170 is threaded onto the core wire 120 followed by the proximal filter core tube 140, and the filter element 135 is advanced to the core wire tip 110 in a collapsed state. The hypo shaft 130 is then slid along the core wire 120 until a distal end of the hypo shaft 130 approaches the proximal end of the proximal filter core tube 140. The guidewire 100, thus prepared, is then inserted into a vasculature and the guidewire 100, with the filter element 135 thereon, is advanced within the vasculature until the filter element 135 is correctly positioned downstream from a treatment area using a method known in the art, i.e., until a proximal end of the core wire tip 110 is downstream of a treatment area. The hypo shaft 130 is then slid in a distal direction by pushing on the hypo shaft 130 from a proximal end thereof and holding the core wire 120 steady until the distal end of the hypo shaft 130 meets the proximal end of the proximal filter core tube 140, thereby engaging the filter element 135. Thus engaged, the hypo shaft 130 is pushed proximally further along with the filter element 135 until the distal filter core tube 170 meets the core wire tip 110. By pushing the hypo shaft 130 even further from the proximal end thereof, the filter element 135 is deployed into an expanded state. A treatment catheter may then be threaded over the hypo shaft 130 using the hypo shaft 130 as a guidewire therefor.

Alternatively, the guidewire 100 may also be used with a delivery catheter to deliver the filter element 135 onto the core wire 120. In this exemplary embodiment, the hypo shaft 130 wire 120 is slid along the core wire 120 until a distal end of the hypo shaft meets the core wire tip 110. The guidewire 110 is then inserted into a vasculature and the hypo shaft 130 is moved through the vasculature until a proximal end of the core wire tip 110 is downstream of a treatment area. The hypo shaft 130 is then slid in a proximal direction by pulling the hypo shaft 130 from a proximal end thereof to form a filter location space L between a distal end of the hypo shaft 130 and the core wire tip 110. A delivery catheter, containing an embolic protection device therein, is slid coaxially along the hypo shaft 130 until a proximal end of the embolic protection device passes a distal end of the hypo shaft 130. The delivery catheter is then pulled a proximal end thereof to deploy the embolic protection device causing the embolic protection device to be left on the core wire 120 where it made contact with the distal end of the hypo shaft 130. The delivery catheter is then removed from the vasculature.

With the embolic protection device thus deployed, the hypo shaft 130 may be moved proximally as desired to allow the core wire 120 to move without affecting the position of the embolic protection device.

The foregoing exemplary embodiments and advantages are merely exemplary and are not to be construed as limiting the present invention. The present teaching can be readily applied to other types of apparatuses. Also, the description of the exemplary embodiments of the present invention is intended to be illustrative, and not to limit the scope of the claims, and many alternatives, modifications, and variations will be apparent to those skilled in the art.

What is claimed is:

1. A method of using a guidewire which includes a core wire, a core wire tip disposed at a distal end of the core wire, and a hypo shaft, moveably and coaxially disposed around the core wire, the method comprising:

sliding the hypo shaft along the core wire until a distal end of the hypo shaft meets the core wire tip;

inserting the hypo shaft into a vasculature and moving the hypo shaft through the vasculature until a proximal end of the core wire tip is downstream of a treatment area;

sliding the hypo shaft in a proximal direction from a proximal end thereof to form a filter location space between a distal end of the hypo shaft and the core wire tip;

sliding a delivery sheath, containing an embolic protection device therein, coaxially along the hypo shaft until a proximal end of the embolic protection device passes a distal end of the hypo shaft;

pulling the delivery sheath from a proximal end thereof to deploy the embolic protection device into the filter location space; and removing the delivery sheath from the vasculature.

2. The method of claim 1, further comprising sliding a treatment device coaxially over the hypo shaft after the embolic protection device is deployed.

3. The method of claim 2, wherein the treatment device comprises a catheter.

4. The method of claim 1, wherein after the embolic protection device is deployed, the hypo shaft may be moved proximally or distally as desired to allow the core wire to move without effecting the position of the embolic protection device.

* * * * *